United States Patent
Encarnacion et al.

(10) Patent No.: US 11,707,067 B2
(45) Date of Patent: *Jul. 25, 2023

(54) HAIR GROOMING IMPLEMENT CLEANING SOLUTION WITH STABILIZER

(71) Applicant: ZAE Products & Services LLC, Thiells, NY (US)

(72) Inventors: Zoraida Encarnacion, Theills, NY (US); Jiangyin Bao, Ann Arbor, MI (US); Hansini Mundigala, Ypsilanti, MI (US)

(73) Assignee: ZAE PRODUCTS & SERVICES LLC, Thiells, NY (US)

( * ) Notice: Subject to any disclaimer, the term of this patent is extended or adjusted under 35 U.S.C. 154(b) by 70 days.

This patent is subject to a terminal disclaimer.

(21) Appl. No.: 16/393,673

(22) Filed: Apr. 24, 2019

(65) Prior Publication Data

US 2019/0261632 A1   Aug. 29, 2019

Related U.S. Application Data

(63) Continuation-in-part of application No. 15/097,584, filed on Apr. 13, 2016, now Pat. No. 10,314,310.

(51) Int. Cl.
| | | |
|---|---|---|
| A01N 59/00 | (2006.01) | |
| A01N 25/22 | (2006.01) | |
| C11D 3/48 | (2006.01) | |
| C11D 3/395 | (2006.01) | |
| C11D 1/94 | (2006.01) | |
| C11D 3/04 | (2006.01) | |
| A61L 2/18 | (2006.01) | |
| C11D 1/90 | (2006.01) | |
| C11D 1/29 | (2006.01) | |

(52) U.S. Cl.
CPC ............ *A01N 59/00* (2013.01); *A01N 25/22* (2013.01); *A61L 2/18* (2013.01); *C11D 1/94* (2013.01); *C11D 3/044* (2013.01); *C11D 3/3953* (2013.01); *C11D 3/3956* (2013.01); *C11D 3/48* (2013.01); *C11D 1/29* (2013.01); *C11D 1/90* (2013.01)

(58) Field of Classification Search
CPC .... C11D 1/94; C11D 1/29; C11D 1/90; C11D 3/044; C11D 3/3953; C11D 3/3956; C11D 3/48; A61L 2/18; A01N 59/00; A01N 25/22; A01N 25/02; A01N 25/30
See application file for complete search history.

(56) References Cited

U.S. PATENT DOCUMENTS

| | | | | |
|---|---|---|---|---|
| 4,581,148 A | * | 4/1986 | Swanson | C14C 1/06 252/8.57 |
| 10,314,310 B2 | * | 6/2019 | Encarnacion | A01N 59/00 |

\* cited by examiner

*Primary Examiner* — Ali Soroush
(74) *Attorney, Agent, or Firm* — Fowler White Burnett, P.A.

(57) ABSTRACT

A new composition and method for cleaning hair grooming implements is provided. The composition comprises about 1.1% Sodium Hypochlorite, about 2.5% Sodium Hydroxide, about 0.5% Lithium Perchlorate and about 95.9% water. A concentrated version of the solution may be formed and later diluted for use. The addition of surfactant to the solution increases stability and efficiency.

12 Claims, 2 Drawing Sheets

FIGURE 1
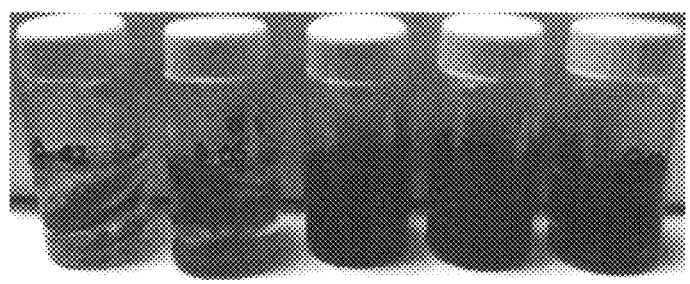
FIGURE 2
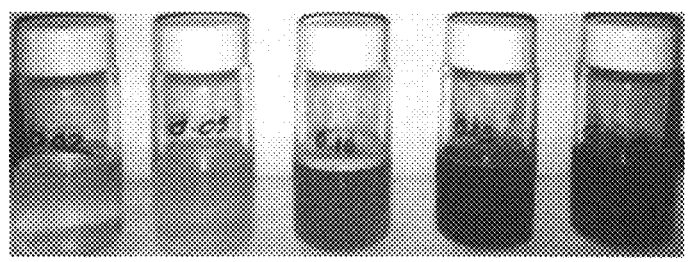
FIGURE 3A          FIGURE 3B          FIGURE 3C
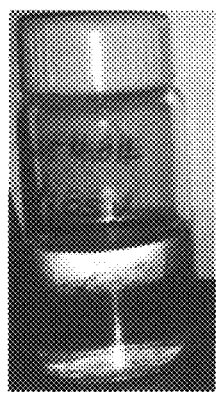 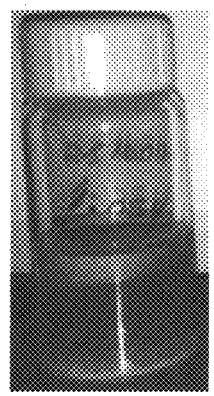 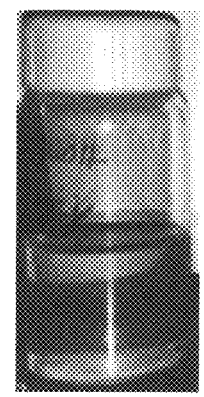

HAIR GROOMING IMPLEMENT CLEANING SOLUTION WITH STABILIZER

CLAIM TO BENEFIT OF A PRIOR-FILED APPLICATION

This continuation in part application claims the benefit of the filing date of patent application Ser. No. 15/097,584 filed on Apr. 13, 2016. Furthermore, all of the claims in the present application claim the benefit of the prior-filed application.

BACKGROUND OF THE INVENTION

1. Field of the Invention

The present invention relates to a solution and method for using a solution for cleaning and disinfecting hair grooming implements such as combs and brushes used by a barber or hair salon stylist. The cleaning and disinfecting solution and the method of its use dissolve hair. Specifically, the present invention relates to a new cleaning composition and a method of using a new cleaning composition comprising at least one compound selected from the group consisting of sodium hypochlorite, sodium hydroxide, and lithium perchlorate in an aqueous solution. Substitute ingredients are also contemplated. The addition of stabilizers and surfactants is also considered.

2. Description of the Related Art

This invention relates to a composition which digests hair. There are drain cleaners which dissolve hair which are known in the market. These cleaners contain sodium or lithium hydroxide and sodium or lithium hypochlorite. However, the known chemical compositions are harsh because they are directed specifically to plumbing applications. The plumbing compositions are not intended, formulated or optimized to be used with hair grooming implements and accessories such as brushes and combs.

In addition, there are solid hair dissolving products that are dissolved in water and then in turn used to dissolve hair. However, these products take too long a time to work for hair care professionals, and they are known to have bad odors.

U.S. Pat. No. 6,136,768 issued to Dawson, et al., is directed to a drain cleaning tablet having a composition which includes chemicals to dissolve hair. However, the composition has high concentrations of both a metal oxide and a hypochlorite generator for actively causing the removal of a greasy or waxy plug from a drain. The high concentrations of the metal oxide and a hypochlorite generator would, in the presence of water, generate large amounts of heat and agitation which would not be acceptable for the business of a haircutter, and certainly not on a shelf or stand in a restricted area where a hair care professional generally operates.

Thus it can be seen that there remains a need for a composition for gently but quickly dissolving hair from an implement such as a comb or brush in a reasonable amount of time. There further is a need for a composition that dissolves hair and disinfects hair grooming implements which may be used with simple protection such as gloves and eye protection, which would ordinarily be used by a hair cutter or stylist for other hair care preparations.

There further is a need for a method and solution which dissolved hair and sediments and disinfects the hair grooming implements and which does not have an offensive odor.

In addition, there is a need for a solution which is made in a concentrated form that is stable for long term storage.

There is also a need for a solution which includes stabilizers to allow storage of the mixed solution.

The present invention has been developed to help address these needs.

SUMMARY OF THE INVENTION

The present invention relates to a method and solution for gently dissolving hair and sediments on hair grooming implements such as combs and brushes used by a barber or hair salon stylist. The method and solution also disinfect the implements.

The present invention provides a method and composition for removing hair from hair grooming implements such as brushes and combs and disinfecting the implements that is gentle so that hair grooming implements may be quickly rinsed and reused by the user giving hair care such as haircutters without the need for bulky chemical safety equipment. The composition would also dissolve hair and sedimented particles within a reasonable time for a brush or comb to be reused by the user. Also, the composition would have sufficient stability so that it may be stored on site at the hair cutter's place of business.

The composition would be nearly odorless.

The method and composition would act as a disinfectant against microbes, including bacteria, protozoa and viruses.

A concentrated formulation is also useful so that it may be diluted by a user to a useful concentration at the time it is to be used.

The solution may be made in a concentrated form which is stable for long term storage.

Stabilizers may be added to allow for storage of a mixed formulation.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated are examples. It is understood that the invention is not limited to the precise arrangements and instrumentalities shown, wherein:

FIG. 1 illustrates samples of different amounts of hair placed in a formulation of the solution of the invention.

FIG. 2 illustrates samples of different amounts of hair placed in a formulation of the solution of the invention after 30 minutes.

FIG. 3A illustrates the amount of dissolution of hair observed immediately after insertion into a formulation of the solution of the invention.

FIG. 3B illustrates the amount of dissolution of hair observed 15 minutes after insertion into a formulation of the solution of the invention.

FIG. 3C illustrates the amount of dissolution of hair observed 30 minutes after insertion into a formulation of the solution of the invention.

DETAILED DESCRIPTION OF THE INVENTION

Figure 4A:
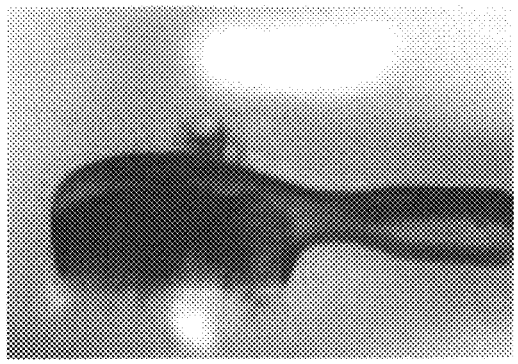
FIG. 4A illustrates a comb with hair entangled in it.

The present invention relates to a successful cleaning and disinfecting solution for hair grooming implements such as combs, brushes and other salon tools.

I. Formulation for Implement Cleaning Solution

One formulation of the solution for cleaning hair grooming implements includes sodium hypochlorite, sodium hydroxide and lithium perchlorate. Water is a solvent for the solution. Efficacy tests were conducted for a solution having the composition provided in Table 1. In the test, 10 ml of the solution effectively digested 0.1 g of human hair and other residues on hair grooming implements within a window of about 30 minutes with minimal safety concerns.

TABLE 1

Formulation for Hair Dissolution

| INGREDIENT | CONCENTRATION BY WEIGHT |
|---|---|
| Sodium Hypochlorite | 1.1% |
| Sodium Hydroxide | 2.5% |
| Lithium Perchlorate | 0.5% |
| Water | 95.9% |

Deionized water was used for testing.

Substitution of ingredients may be made as indicated in Table 2 below:

TABLE 2

Substitute Ingredients

| INGREDIENT AND CONCENTRATION BY WEIGHT | SUBSTITUTION |
|---|---|
| Sodium Hypochlorite 1.1% | Potassium Hypochlorite 1.35% |
| Sodium Hydroxide 2.5% | Potassium Hydroxide 3.5% |
| Lithium Perchlorate 0.5% | Lithium Chlorite 0.27% |

Other substitutions for ingredients having similar chemical properties as the tested ingredients are also contemplated.

Heterogeneous hair samples were used for testing.

Tests confirmed that 10 ml of the formulated implement cleaning solution readily dissolves about 0.05 g of hair in less than 30 minutes of time.

Series of tests were performed on 0.02, 0.05, 0.10, 0.15 and 0.20 grams of hair. Illustrations of the testing of the samples of hair tested are shown in FIG. 1 and FIG. 2.

As shown in FIGS. 1 and 2, about 0.02 grams of hair are shown to be clearly dissolved at 10 mL of the composition described in Table 1. Furthermore, tests confirmed that 10 ml of the formulated solution readily digest about 0.05 g of hair in less than 30 minutes of time FIG. 2. Furthermore, as shown in FIG. 1, a series of tests was performed with varying amounts of the composition of the invention clearly show that 10 ml of the combination described in Table 1 has a capacity to digest about 0.1 g of human hair within a 30 minute time frame.

Also, a range of concentrations were tested for the individual ingredients. The concentrations provided in the given formulation provide the results shown herein.

Also, while slight deviations of the concentrations provided herein will not make significant deviations in the efficacy of the formulation, changes in the ingredient concentrations were determined to affect the time taken to complete the hair digestion. A 10 mL solution with concentrations in Table 1 effectively digests 0.1 g of human hair and other residues on salon tools within a window of 30 minutes. Table 3 below describes the concentrations of ingredients tested:

TABLE 3

Range of Concentrations of Ingredients Tested

| INGREDIENT | RANGE OF CONCENTRATIONS TESTED |
|---|---|
| Sodium Hypochlorite | 0.2% to 10% |
| Sodium Hydroxide | 1.5% to 10% |
| Lithium Perchlorate | 0.1% to 2% |
| Deionized water | N/A |

II. Concentrated Formulation for Cleaning and Disinfecting Solution

A concentrate of the hair grooming implement cleaning solution is formulated for efficient use and ease of handling. The composition of the concentrate (10×) is shown in Table 4 below. The concentrate needs to be diluted before use.

TABLE 4

Formulation for 10x Concentrate

| INGREDIENT | CONCENTRATION BY WEIGHT |
|---|---|
| Sodium Hypochlorite | 11% |
| Sodium Hydroxide | 25% |
| Lithium Perchlorate | 5% |
| Deionized water | 59% |

One method for diluting the concentrated solution is as follows:

Add about 4.5 liters of water into a large container capable of holding at least 5 liters.

Add about 500 ml of the 10× concentrate of the implement cleaning solution to the container.

Agitate the diluted concentrate well before using it.

Allow the concentrate to mix well with the water.

Dip the implements to be cleaned in the solution. The implements may be submerged for full contact with the solution.

Remove the implements after leaving them for 30-45 minutes based on the level of cleaning required.

Rinse the implements thoroughly to remove the intact cleaning solution.

Once the maximum implement limit is reached, the solution may be disposed.

Assuming that there is about 0.1 g of hair left on a hair grooming implement after a single use, and 10 ml are used for each cleaning, the 5 liter solution will be able to clean and disinfect approximately 500 implements.

Other diluted volumes of the cleaning solution are represented in Table 5 below:

TABLE 5

Dilution formulas

| Components | To make the final solution at an approximate total volume | | |
|---|---|---|---|
| | 1 quart | 2 quart | 3 quart |
| 10X concentrate | 3.2 ounce | 6.4 ounce | 9.6 ounce |
| Deionized water | 29 ounce (3 cups and 5 ounce) | 58 ounce (1 quart, 3 cups and 2 ounce) | 87 ounce (2 quart, 2 cups and 7 ounce) |

Figure 4B:
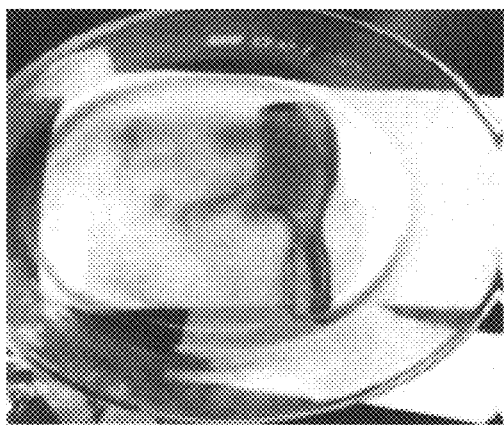
FIG. 4B illustrates a comb with hair entangled in it dipped in approximately 50 ml of a formulation of the solution of the invention.
Figure 4C:
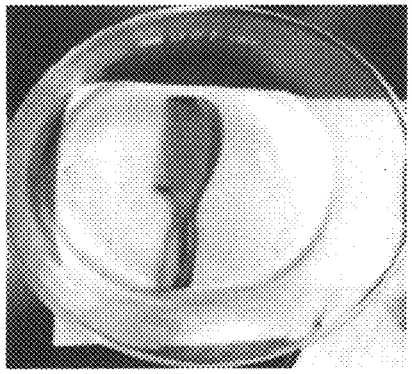
FIG. 4C illustrates a comb after hair and other residues are completely dissolved by a formulation of the solution of the invention.
Figure 4D:
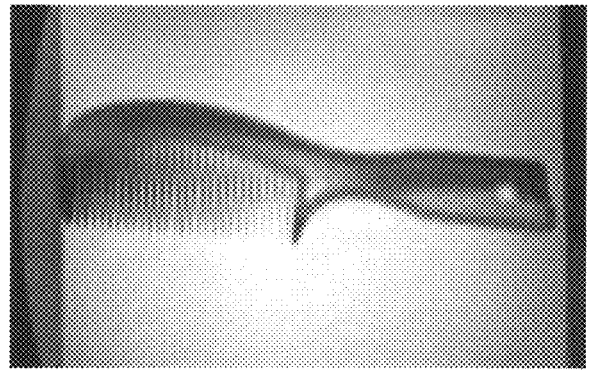
FIG. 4D illustrates a rinsed clean comb removed from a formulation of the solution of the invention.

A method of cleaning implements using a solution of this invention is described herein and illustrated by the use of a comb in FIGS. 4A through 4D. FIG. 4A shows a comb with hair entangled in it. The hair-entangled comb is then placed in the solution. As shown in FIG. 4B, approximately 50 ml may be used for a medium sized comb. The comb is left in the solution for approximately 30 minutes, after which time hair and the other residues were completely digested, as shown in FIG. 4C. The comb may then be removed from the solution and rinsed. The clean comb, shown in FIG. 4D is free from hair and other sediments and ready for another use.

The physical appearance of the formulated 10× concentrated solution is lightly turbid due to the high concentration of solute matter. Upon dilution, the solution appears as a transparent non-turbid solution. Both the concentrate and the final diluted product have very light chlorine smells due to the dissolved active chlorine. However, the odor is so slight that it is close to odorless. Upon consumption of the active chlorine in the solution, the solution acquires a brown coloration and it is an indication that the maximum cleaning capacity has reached, as illustrated in the fifth vial in FIG. 2. Implements may be thoroughly washed with water to remove the intact cleaning solution prior to use on a person.

The formulated solution has been proven to cleanse implements from trapped hair and other sedimented particles after exposing the implements to the formulated solution for approximately 30 minutes. In addition to cleaning the implements by dissolving hair and sediments, the active chlorine in the solution helps disinfect the implement. Also, the active chlorine may inactivate all types of microbes including bacteria, protozoa and viruses.

The formulated solution will have similar stability to regular household liquid bleach and may be stored accordingly, such as at room temperature in closed container, away from direct sunshine and heat.

The addition of a stabilizer such as a surfactant mixture increases the stability and efficiency of the solution. The surfactant may be an anionic surfactant or other surfactant known in the art.

Furthermore, the presence of surfactants in the formulation adds the detergency or soil removal to the original formulation. Sodium hypochlorite itself retains excellent stability in the presence of anionic surfactants. A surfactant mixture composed of sodium lauryl sulfate and cocamidopropyl betaine, at between approximately 0.1% to 1% by weight concentration when mixed with a 10× concentrated solution, when then used in the diluted formulation, maintained or even enhanced the stability and efficiency of the formulation compared with a freshly made formulation. The addition of surfactant cocamidopropyl betaine alone does not have any significant effect on the stability.

As shown in Tables 6 and 7 below, the inclusion of approximately 0.05% by weight to the mixture for the non-concentrated formulation is enough to provide increased stability and efficiency. Substitute ingredients discussed above would also be substitutable for the embodiment of this invention including a stabilizer. Inclusion of a stabilizer such as a surfactant for the concentrated formulation also increases stability and efficiency:

TABLE 6

Formulation for Increased Stability and Efficiency
(Non-Concentrated Formulation)

| INGREDIENT | CONCENTRATION BY WEIGHT |
|---|---|
| Sodium Hypochlorite | 1.1% |
| Sodium Hydroxide | 2.5% |
| Lithium Perchlorate | 0.5% |
| Surfactant Mixture | 0.05% |
| Deionized water | 95.85% |

TABLE 7

Formulation for Increased Stability and Efficiency
(Concentrated Formulation)

| INGREDIENT | CONCENTRATION BY WEIGHT |
|---|---|
| Sodium Hypochlorite | 11% |
| Sodium Hydroxide | 25% |
| Lithium Perchlorate | 5% |
| Surfactant Mixture | 0.5% |
| Deionized water | 58.5% |

As stated above, one effective stabilizer inclusion to the formulation is the addition of 0.5% by weight surfactant mixture of sodium lauryl sulfate and cocamidopropyl betaine, or their equivalents. For example, Calblend® DF manufactured by Pilot Chemical Company may be used.

In addition, storage under dark conditions to avoid exposure to UV light, as well as storage at temperatures in the range of 59-77° F. significantly increases the stability and helps to retain the hair digestibility efficacy of the formulation.

Other means for increasing the stability and the ability to store a caustic compound known in the art are also contemplated.

TABLE 8

Ingredient Quantity Estimation Based On Variable Production Quantities for the Final 10X Concentrate

| Vol. of Concentrate 10X | Quantity of Ingredients | | | | | | | |
|---|---|---|---|---|---|---|---|---|
| | Sodium Hypochlorite (g) | Lithium Perchlorate (g) | Sodium Hydroxide (g) | Surfactant Mixture (g) | Distilled Water* | | | |
| | | | | | Oz | Cup (8 oz) | Quart (32 oz) | Gallon (128 oz) |
| ½ Cup (4 oz) | 13.0 | 5.9 | 29.6 | 0.6 | 3.7 | 0.46 | 0.11 | 0.03 |
| ¾ Cup (6 oz) | 19.5 | 8.9 | 44.4 | 0.9 | 5.5 | 0.69 | 0.17 | 0.04 |
| 1 Cup (8 oz) | 26.1 | 11.8 | 59.2 | 1.2 | 7.4 | 0.92 | 0.23 | 0.06 |
| 1½ Cups (12 oz) | 39.0 | 17.7 | 88.7 | 1.8 | 11.1 | 1.39 | 0.35 | 0.09 |
| 2 Cups (16 oz) | 52.1 | 23.7 | 118.3 | 2.4 | 14.8 | 1.85 | 0.46 | 0.12 |
| 1 Bottle (25.3 oz) | 82.5 | 37.5 | 187.5 | 3.8 | 23.5 | 2.94 | 0.73 | 0.18 |

As shown in Table 8 above, there is some variation in the quantity of the ingredients of the concentrated formulation which will still result in an efficacious formulation. Thus, there is also variation in the quantity of the ingredients of the diluted formulation which will still result in an efficacious formulation.

It will be appreciated by persons skilled in the art that the present invention is not limited to what has been particularly shown and described herein above. In addition, unless mention was made above to the contrary, it should be noted that the accompanying drawings are not to scale. A variety of modifications and variations are possible in light of the above teachings without departing from the scope and spirit of the invention.

What is claimed is:

1. A hair grooming implement cleaning and disinfecting composition which dissolves hair, comprising:
    a. at least one of Sodium Hypochlorite and Potassium Hypochlorite,
    b. at least one of Sodium Hydroxide and Potassium Hydroxide,
    c. at least one of Lithium Perchlorate and Lithium Chlorite, and
    d. a surfactant,
    in an aqueous solution wherein concentrations of composition elements a., b. and c. are sufficient in the aqueous solution so that the composition has the ability to dissolve approximately 0.05 grams of hair in approximately 30 minutes.

2. The composition of claim 1, wherein the Sodium Hypochlorite is between 0.2 and 10 percent by weight of the solution.

3. The composition of claim 1, wherein the Sodium Hydroxide is between 1.5 and 10 percent by weight of the solution.

4. The composition of claim 1, wherein the Lithium Perchlorate is between 0.1 and 2 percent by weight of the solution.

5. The composition of claim 1, wherein the surfactant between 0.1 and 1 percent by weight of the solution.

6. A hair grooming implement cleaning and disinfecting composition, comprising a component mixture of:
    about 1.1% by weight Sodium Hypochlorite;
    about 2.5% by weight Sodium Hydroxide;
    about 0.5% by weight Lithium Perchlorate; and
    about 0.05% by weight stabilizer;
    in an aqueous solution.

7. A hair grooming implement cleaning and disinfecting composition, comprising a component mixture of:
    about 1.35% by weight Potassium Hypochlorite;
    about 2.5% by weight Potassium Hydroxide;
    about 0.5% by weight Lithium Chlorite; and
    about 0.05% by weight stabilizer;
    in an aqueous solution.

8. A hair grooming implement cleaning and disinfecting method, comprising the steps of:
    a. providing a solution comprising a component mixture of:
        at least one of Sodium Hypochlorite and Potassium Hypochlorite,
        at least one of Sodium Hydroxide and Potassium Hydroxide,
        at least one of Lithium Perchlorate and Lithium Chlorite, and
        a stabilizer
        in an aqueous solution;
    b. placing at least a portion of hair grooming implement in contact the solution; and
    c. allowing the hair grooming implement to remain in contact with the solution for a sufficient time to dissolve hair or sediment on the implement.

9. The method of claim 8, wherein the sufficient time is approximately 30 minutes.

10. A concentrated hair grooming implement cleaning and disinfecting composition, comprising a component mixture of:
    about 11% by weight Sodium Hypochlorite;
    about 25% by weight Sodium Hydroxide;
    about 5% by weight Lithium Perchlorate;
    about 0.5% by weight stabilizer;
    in an aqueous solution.

11. The composition of claim 10, wherein the stabilizer comprises a surfactant.

12. The composition of claim 11, wherein the surfactant comprises sodium lauryl sulfate and cocamidopropyl betaine.

* * * * *